US011951114B2

(12) United States Patent
Lian et al.

(10) Patent No.: US 11,951,114 B2
(45) Date of Patent: *Apr. 9, 2024

(54) USE OF THYROID BETA-AGONISTS

(71) Applicants: Viking Therapeutics, Inc., San Diego, CA (US); Metabasis Therapeutics, Inc., San Diego, CA (US)

(72) Inventors: Brian Lian, San Diego, CA (US); Rochelle Hanley, Ann Arbor, MI (US); Misha Dinerman, Cincinnati, OH (US); Mark Erion, Brookline, MA (US); Serge Boyer, San Diego, CA (US); Hongjian Jiang, Shanghai (CN)

(73) Assignees: Viking Therapeutics, Inc., San Diego, CA (US); Metabasis Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,621

(22) Filed: May 6, 2022

(65) Prior Publication Data

US 2022/0257618 A1 Aug. 18, 2022

Related U.S. Application Data

(63) Continuation of application No. 16/095,228, filed as application No. PCT/US2017/029120 on Apr. 24, 2017, now Pat. No. 11,351,183.

(60) Provisional application No. 62/326,436, filed on Apr. 22, 2016.

(51) Int. Cl.
*A61K 31/662* (2006.01)

(52) U.S. Cl.
CPC .................................. *A61K 31/662* (2013.01)

(58) Field of Classification Search
CPC ........................................................ A61K 31/662
See application file for complete search history.

(56) References Cited

U.S. PATENT DOCUMENTS

| 7,514,419 | B2 | 4/2009 | Erion et al. |
| 7,829,552 | B2 | 11/2010 | Erion et al. |
| 9,970,006 | B2 | 5/2018 | Bettencourt et al. |
| 11,351,183 | B2 | 6/2022 | Lian et al. |
| 2009/0042857 | A1 | 2/2009 | Yamaoka et al. |
| 2009/0232879 | A1 | 9/2009 | Cable et al. |
| 2011/0071208 | A1 | 3/2011 | MacLachlan et al. |

FOREIGN PATENT DOCUMENTS

| CA | 2543132 | A1 | 5/2005 | |
| CN | 1886131 | A | 12/2006 | |
| CN | 101072555 | A | 11/2007 | |
| JP | 2019-507069 | A | 3/2019 | |
| WO | WO-2006128056 | A2 * | 11/2006 | ............ C07F 9/301 |
| WO | WO-2011/038207 | A1 | 3/2011 | |
| WO | WO-2011038207 | A1 * | 3/2011 | ............ A61K 31/662 |
| WO | WO-2014/178892 | A1 | 11/2014 | |
| WO | WO-2016/134292 | A1 | 8/2016 | |
| WO | WO-2017/185083 | A1 | 10/2017 | |
| WO | WO-2017/201320 | A1 | 11/2017 | |

OTHER PUBLICATIONS

Genin et al. (J of Steroid Biochemistry and Molecular Biology, 2009, 37-43) (Year: 2009).*
Fourcade et al. (Molecular Pharmacology, 63, 6, 2003, 1296-1303). (Year: 2003).*
Engelen et al., "Bezafibrate for X-Linked Adrenoleukodystrophy," Plos One, 7(7): e41013 (2012).
Engelen et al., "Lovastatin in X-Linked Adrenoleukodystrophy," The New England Journal of Medicine 362(3): 276-277 ( 2010).
Engelen et al., "X-linked adrenoleukodystrophy (X-ALD): clinical presentation and guidelines for diagnosis, follow-up and management," Orpanet Journal of Rare Disease, 7(51): 1-14 (2012).
Engelen et al., "X-Linked Adrenoleukodystrophy: Pathogenesis and Treatment," Current Neurology and Neuroscience Reports, 14(10): 486 (2014).
Erion et al., "Targeting thyroid hormone receptor-β agonists to the liver reduces cholesterol and triglycerides and improves the therapeutic index," PNAS, 104(39): 15490-15495 (2007).
Extended European Search Report for EP Application No. EP 17786795 dated Feb. 25, 2020.
Extended European Search Report for EP Application No. EP 17786798 dated Nov. 18, 2019.
Fourcade et al., "Fibrate induction of the adrenoleukodystrophy? related gene (ABCD2) Promoter analysis and role of the peroxisome proliferator-activated receptor PPARα," European Journal of Biochemistry, 268(12): 3490-3500 (2001).
Fourcade et al., "Thyroid Hormone Induction of the Adrenoleukodystrophy-Related Gene (ABCD2)," Molecular Pharmacology, 63(6): 1296-1303 (2003).
Genin et al., "Induction of the adrenoleukodystrophy-related gene (ABCD2) by thyromimetics," J Steroid Biochem Mol Biol, 116(1-2):37-43 (2009).
Gondcaille et al., "Phenylbutyrate up-regulates the adrenoleukodystrophy-related gene as a nonclassical peroxisome proliferator," Journal of Cell Biology, 169(1): 93-104 (2005).
International Preliminary Report on Patentability for International Application No. PCT/US2017/029102 dated Oct. 23, 2018.
International Search Report and Written Opinion for International Application No. PCT/US2017/029102 dated Jul. 30, 2017.
International Search Report and Written Opinion for International Application No. PCT/US2017/029120 dated Jul. 26, 2017.
International Search Report and Written Opinion for International Application No. PCT/US2017/029120 dated Oct. 23, 2018.
Jin et al., "Peroxisome profilerator activated receptor gamma and thyroid associated ophthalmopathy," International Journal of Pathology and Clinical Medicine, 30(6): 531-535 w/ English Abstract (2010).
Kemp et al., "Biochemical Aspects of X-Linked Adrenoleukodystrophy," Brain Pathology, 20(4): 831-837 (2010).
Li et al., "Review of the hotspots of the 67th meeting of the American Diabetes Association," Journal of Practical Diabetology, 5(2): 7-9 w/ Machine Generated Translation (2008).

(Continued)

*Primary Examiner* — Umamaheswari Ramachandran
(74) *Attorney, Agent, or Firm* — Foley Hoag LLP; David P. Halstead; Benjamin A. Vaughan

(57) ABSTRACT

Methods useful for treating X-linked adrenoleukodystrophy are provided.

6 Claims, 10 Drawing Sheets

(56) References Cited

OTHER PUBLICATIONS

Pujol., "Novel Therapeutic Targets and Drug Candidates for Modifying Disease Progression in Adrenoleukodystrophy," Advanced Therapies in Pediatric Endocrinology, 30: 147-160 (2016).
Singh et al., "Lovastatin for X-Linked Adrenoleukodystrophy," The New England Journal of Medicine, 339: 702-703 (1998).
Weber et al., "Evaluation of Retinoids for Induction of the Redundant Gene ABCD2 as an Alternative Treatment Option in X-linked Adrenoleukodystrophy," Plos One, 9(7): e103742 (2014).

* cited by examiner

USE OF THYROID BETA-AGONISTS

RELATED APPLICATIONS

This application is a continuation of U.S. patent application Ser. No. 16/095,228, filed Oct. 19, 2018; which is a U.S. National Stage of International Patent Application No. PCT/US2017/029120, filed Apr. 24, 2017, which claims the benefit of priority to U.S. Provisional Patent Application Ser. No. 62/326,436, filed Apr. 22, 2016, the contents of each of which are hereby incorporated by reference in their entirety.

BACKGROUND

Adrenoleukodystrophy (also known as X-linked adrenoleukodystrophy, X-ALD) is a disorder of peroxisomal fatty acid beta oxidation which results in the accumulation of very long chain fatty acids in tissues throughout the body. The most severely affected tissues are the myelin in the central nervous system, the adrenal cortex, and the Leydig cells in the testes. As an X-linked disorder, X-ALD primarily manifest in males; however, approximately 50% of heterozygote females show some symptoms later in life. The most severe form of X-ALD is known as cerebral ALD, and is characterized by a rapidly progressive inflammatory demyelination process in brain tissue. This form is more common in early childhood, typically presenting in children under the age of 12. Patients with cerebral ALD typically experience rapid degeneration to a vegetative state within 3 to 5 years. The more common form of X-ALD is known as adrenomyeloneuropathy (AMN). This form of the disease manifests later in life, typically between the ages of 25 and 45. AMN affects the spinal cord and motor neurons, but has no inflammatory component or brain involvement. AMN patients first present with trouble walking leading to progressive motor impairment with leg paralysis.

ALD is caused by mutations in the gene for the ATP-Binding Cassette transporter dl (ABCD1) located on the X chromosome. ABCD1 functions to transport very long chain fatty acids (VLCFA) into peroxisome for degradation. In X-ALD, defective ABCD1 leads to the accumulation of VLCFA. Individuals with X-ALD show very high levels of unbranched, saturated, very long chain fatty acids, particularly cerotic acid (26:0). Treatment options for X-ALD are limited as there is no cure and no approved therapy.

Thus, there is a need for improved methods for treating X-ALD.

SUMMARY

Provided herein are methods for treating X-linked adrenoleukodystrophy, comprising administering to a subject a compound having the structure

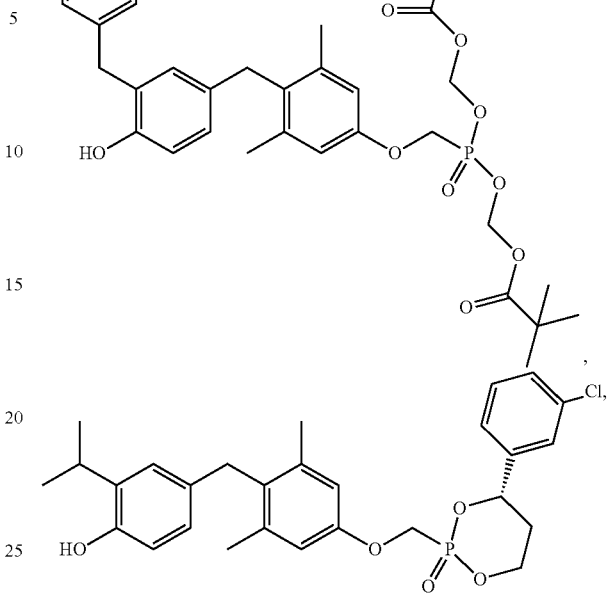

or a salt, ester, or prodrug thereof. In certain embodiments, the compound is administered at a dose of 5 mg/day, 10 mg/day, 10 mg every other day, or 15 mg every other day.

In certain embodiments, the compound is administered daily, every other day, or intermittently for three months followed by a period of time of one month when the pharmaceutical composition is not administered.

DETAILED DESCRIPTION

Figure 1:
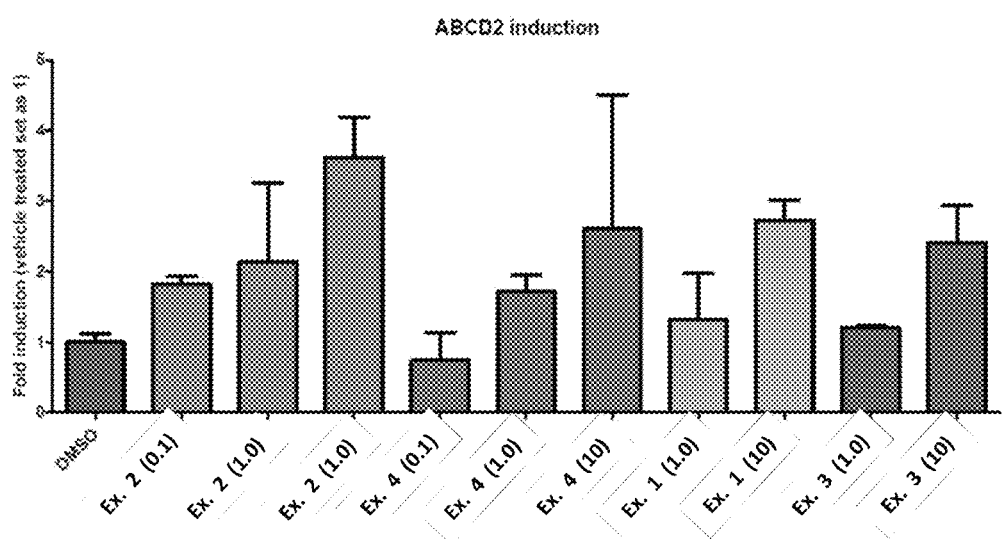
FIG. 1 is a bar graph showing the effect of the assayed compounds on ABCD2 expression. The numbers in parenthesis indicate concentration of the respective compound in 04.

In certain aspects, provided herein are methods related to the treatment of x-linked adrenoleukodystrophy (X-ALD). In certain aspects, the invention provides methods of treating X-ALD, comprising administering to a subject a compound (e.g., a thyroid hormone receptor beta agonist), e.g., in a therapeutically effective amount.

In certain embodiments, a thyroid receptor beta agonist is a phosphonic acid containing compound or salt, ester, or prodrug thereof, such as those disclosed in U.S. Pat. No. 7,829,552 and U.S. Patent Publication 2009-0232879, hereby incorporated by reference in their entireties, and specifically with respect to the compounds and prodrugs disclosed therein. In certain embodiments, the thyroid receptor beta agonist is a compound of Formula I:

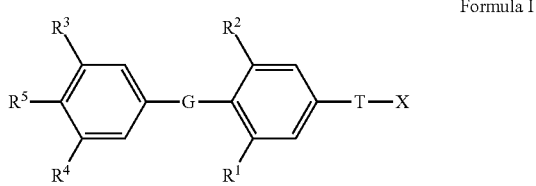

Formula I wherein:
G is selected from the group consisting of —O—, —S(O)$_a$—, —CH$_2$—, —CF$_2$—, —CHF—, —C(O)—, —CH(OH)—, —NH—, and —N(C$_1$-C$_4$ alkyl)-;
a is an integer from 0 to 2;
T is selected from the group consisting of —(CR$^a{}_2$)$_m$—, —CH=CH—, —O(CR$^b{}_2$)(CR$^a{}_2$)$_p$—, —S(CR$^b{}_2$)(CR$^a{}_2$)$_p$—, —N(R$^b$)(CR$^b{}_2$)(CR$^a{}_2$)$_p$—, —N(R$^b$)C(O)(CR$^a{}_2$)$_p$—, —(CR$^a{}_2$)$_p$CH(NR$^c{}_2$)—, —C(O)(CR$^a{}_2$)$_p$—, —(CR$^a{}_2$)$_n$C(O)—, —(CR$^a{}_2$)C(O)(CR$^a{}_2$)—, and —C(O)NH(CR$^b{}_2$)—;
m=0-3;
n=0-2;
p=0-1;
each R$^a$ is independently selected from the group consisting of hydrogen, optionally substituted —C$_1$-C$_4$ alkyl, halogen, —OH, optionally substituted —O—C$_1$-C$_4$ alkyl, —OCF$_3$, optionally substituted —S—C$_1$-C$_4$ alkyl, —NR$^c{}_2$, optionally substituted —C$_2$-C$_4$ alkenyl, and optionally substituted —C$_2$-C$_4$ alkynyl;
each R$^b$ is independently selected from the group consisting of hydrogen, optionally substituted —C$_1$-C$_4$ alkyl, optionally substituted —C$_2$-C$_4$ alkenyl, and optionally substituted —C$_2$-C$_4$ alkynyl;
each R$^c$ is independently selected from the group consisting of hydrogen, optionally substituted —C$_1$-C$_4$ alkyl, optionally substituted —C$_2$-C$_4$ alkenyl, optionally substituted —C$_2$-C$_4$ alkynyl, and optionally substituted —C(O)—C$_1$-C$_4$ alkyl;
R$^1$ and R$^2$ are each independently selected from the group consisting of halogen, optionally substituted —C$_1$-C$_4$ alkyl, optionally substituted —S—C$_1$-C$_3$ alkyl, optionally substituted —C$_2$-C$_4$ alkenyl, optionally substituted —C$_2$-C$_4$ alkynyl, —CF$_3$, —OCF$_3$, optionally substituted-O—C$_1$-C$_3$ alkyl, and cyano;
R$^3$ and R$^4$ are each independently selected from the group consisting of hydrogen, halogen, —CF$_3$, —OCF$_3$, cyano, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_m$aryl, optionally substituted (CR$^a{}_2$)$_m$cycloalkyl, optionally substituted (CR$^a{}_2$)$_m$heterocycloalkyl, —OR$^d$, —SR$^d$, —S(O)$_{1-2}$R$^e$, —S(O)$_2$NR$^f$R$^g$, —C(O)NR$^f$R$^g$, —C(O)OR$^h$, —C(O)R$^e$, —N(R$^b$)C(O)R$^e$, —N(R$^b$)C(O)NR$^f$R$^g$, —N(R$^b$)S(O)$_2$R$^e$, —N(R$^b$)S(O)$_2$NR$^f$R$^g$, and —NR$^f$R$^g$;
each R$^d$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted, —(CR$^b{}_2$)$_n$aryl, optionally substituted —(CR$^b{}_2$)$_n$cycloalkyl, optionally substituted —(CR$^b{}_2$)$_n$heterocycloalkyl, and —C(O)NR$^f$R$^g$;
each R$^e$ is selected from the group consisting of optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^a{}_2$)$_n$aryl, optionally substituted, —(CR$^a{}_2$)$_n$cycloalkyl, and optionally substituted —(CR$^a{}_2$)$_n$heterocycloalkyl;
R$^f$ and R$^g$ are each independently selected from the group consisting of hydrogen, optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl, or R$^f$ and R$^g$ may together form an optionally substituted heterocyclic ring, which may contain a second heterogroup selected from the group of O, NR$^b$, and S, wherein any substituents up to four are selected from the group consisting of optionally substituted —C$_1$-C$_4$ alkyl, —OR$^b$, oxo, cyano, —CF$_3$, optionally substituted phenyl, and —C(O)OR$^h$;
each R$^h$ is optionally substituted —C$_1$-C$_{12}$ alkyl, optionally substituted —C$_2$-C$_{12}$ alkenyl, optionally substituted —C$_2$-C$_{12}$ alkynyl, optionally substituted —(CR$^b{}_2$)$_n$aryl, optionally substituted —(CR$^b{}_2$)$_n$cycloalkyl, and optionally substituted —(CR$^b{}_2$)$_n$heterocycloalkyl;
R$^5$ is selected from the group consisting of —OH, optionally substituted —OC$_1$-C$_6$ alkyl, —OC(O)R$^e$, —F, —NHC(O)R$^e$, —NHS(O)$_{1-2}$R$^e$, —NHC(S)NH(R$^h$), and —NHC(O)NH(R$^h$);
X is P(O)YR$^{11}$Y'R$^{11}$;
Y and Y' are each independently selected from the group consisting of —O—, and —NR$^v$—;
when Y and Y' are —NR$^v$—, then R$^{11}$ attached to —NR$^v$— is independently selected from the group consisting of —H, —[C(R$^z$)$_2$]$_q$—COOR$^y$, —C(R$^x$)$_2$COOR$^y$, —[C(R$^z$)$_2$]$_q$—C(O)SR$^y$, and -cycloalkylene-COOR$^y$;
when Y and Y' are —O—, R$^{11}$ attached to —O— is independently selected from the group consisting of —H, alkyl, optionally substituted aryl, optionally substituted heterocycloalkyl, optionally substituted CH$_2$-heterocycloakyl wherein the cyclic moiety contains a carbonate or thiocarbonate, optionally substituted -alkylaryl, —C(R$^z$)$_2$OC(O)NR'2, —NW—C(O)—R$^y$, —C(R$^z$)$_2$—OC(O)R$^y$, —C(R$^z$)$_2$—O—C(O)OR$^y$, —C(R$^z$)$_2$OC(O)SR$^y$, -alkyl-S—C(O)R$^y$, -alkyl-S—S-alkylhydroxy, and -alkyl-S—S-alkylhydroxy; or
together R$^{11}$ and R$^{11}$ are -alkyl-S—S-alkyl- to form a cyclic group, or together R$^{11}$ and R$^{11}$ are the group:

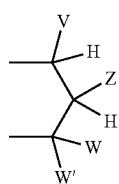

wherein:
V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl;

together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH=CR$^z{}_2$)OH, —CH(C≡CR$^z$)OH, —R$^z$, —NR$^z{}_2$, —OCOR$^y$, —OCO$_2$R$^y$, —SCOR$^y$, —SCO$_2$R$^y$, —NHCOR$^z$, —NHCO$_2$R$^y$, —CH$_2$NH aryl, —(CH$_2$)$_q$—OR$^z$, and —(CH$_2$)$_q$—SW;

q is an integer 2 or 3;
with the provisos that:
a) V, Z, W, W' are not all —H; and
b) when Z is —R$^z$, then at least one of V, W, and W' is not —H, alkyl, aralkyl, or heterocycloalkyl;

each R$^z$ is selected from the group consisting of R$^y$ and —H;
each R$^y$ is selected from the group consisting of alkyl, aryl, heterocycloalkyl, and aralkyl;
each R$^x$ is independently selected from the group consisting of —H, and alkyl, or together R$^x$ and R$^x$ form a cyclic alkyl group;

each R$^v$ is selected from the group consisting of —H, lower alkyl, acyloxyalkyl, alkoxycarbonyloxyalkyl, and lower acyl;
and pharmaceutically acceptable salts and prodrugs thereof and pharmaceutically acceptable salts of the prodrugs.

when G is —O—, T is —CH$_2$—, R$^1$ and R$^2$ are bromo, R$^3$ is iso-propyl, R$^4$ is hydrogen, and R$^5$ is —OH, then X is not P(O)(OH)$_2$ or P(O)(OCH$_2$CH$_3$)$_2$;
or a salt, ester, or prodrug thereof.

In certain embodiments, G is selected from the group consisting of —O— and —CH$_2$—.

In certain embodiments, R$^5$ is selected from —OH, optionally substituted —OC$_1$-C$_6$ alkyl, and —OC(O)R$^e$.

In certain embodiments, R$^4$ is selected from hydrogen, halogen, —CF$_3$, —OCF$_3$, cyano, optionally substituted —C$_1$-C$_{12}$ alkyl, optionally substituted —C$_2$-C$_{12}$ alkenyl, and optionally substituted —C$_2$-C$_{12}$ alkynyl.

In certain embodiments, wherein T is —O(CR$^b{}_2$)(CR$^a{}_2$)$_p$—, and p is 0 or 1.

In certain embodiments, Y and Y' are —O—, R$^{11}$ attached to —O— is independently selected from the group consisting of —H, alkyl, optionally substituted aryl, optionally substituted heterocycloalkyl, and —C(R$^z$)$_2$—OC(O)R$^y$.

In certain embodiments, when Y and Y' are —O— together R$^{11}$ and R$^{11}$ form the group:

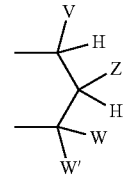

wherein:
V, W, and W' are independently selected from the group consisting of hydrogen, optionally substituted alkyl, optionally substituted aralkyl, heterocycloalkyl, aryl, substituted aryl, heteroaryl, substituted heteroaryl, optionally substituted 1-alkenyl, and optionally substituted 1-alkynyl;

or together V and Z are connected via an additional 3-5 atoms to form a cyclic group containing 5-7 atoms, wherein 0-1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or together V and Z are connected via an additional 3-5 atoms to form a cyclic group, wherein 0-1 atoms are heteroatoms and the remaining atoms are carbon, that is fused to an aryl group at the beta and gamma position to the Y attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3-5 atoms to form a cyclic group, wherein 0-1 atoms are heteroatoms and the remaining atoms are carbon, and V must be aryl, substituted aryl, heteroaryl, or substituted heteroaryl;

together W and W' are connected via an additional 2-5 atoms to form a cyclic group, wherein 0-2 atoms are heteroatoms and the remaining atoms are carbon, and V must be aryl, substituted aryl, heteroaryl, or substituted heteroaryl;

Z is selected from the group consisting of —CHR$^z$OH, —CHR$^z$OC(O)R$^y$, —CHR$^z$OC(S)R$^y$, —CHR$^z$OC(S)OR$^y$, —CHR$^z$OC(O)SR$^y$, —CHR$^z$OCO$_2$R$^y$, —OR$^z$, —SR$^z$, —CHR$^z$N$_3$, —CH$_2$aryl, —CH(aryl)OH, —CH(CH═CR$^z{}_2$)OH, —CH(C≡CR$^z$)OH, —R$^z$, —NR$^z{}_2$, —OCOR$^y$, —OCO$_2$R$^y$, —SCOR$^y$, —SCO$_2$R$^y$, —NHCOR$^z$, —NHCO$_2$R$^y$, —CH$_2$NH aryl, —(CH$_2$)$_q$—OR$^z$, and —(CH$_2$)$_q$—SW;

q is an integer 2 or 3;

with the provisos that:

a) V, Z, W, W' are not all —H; and b) when Z is —R$^z$, then at least one of V, W, and W' is not —H, alkyl, aralkyl, or heterocycloalkyl;

each R$^z$ is selected from the group consisting of R$^y$ and —H;

each R$^y$ is selected from the group consisting of alkyl, aryl, heterocycloalkyl, and aralkyl;

each R$^x$ is independently selected from the group consisting of —H, and alkyl, or together R$^x$ and R$^x$ form a cyclic alkyl group;

each R$^v$ is selected from the group consisting of —H, lower alkyl, acyloxyalkyl, alkoxycarbonyloxyalkyl, and lower acyl.

In certain embodiments, V is substituted aryl, and W and W' are hydrogen.

In certain preferred embodiments, the thyroid hormone receptor beta agonist is a compound as shown in Table I or a salt, ester, or prodrug thereof.

TABLE 1

Exemplary Thyroid Receptor beta Agonists

| Example | Structure |
|---|---|
| 1 | 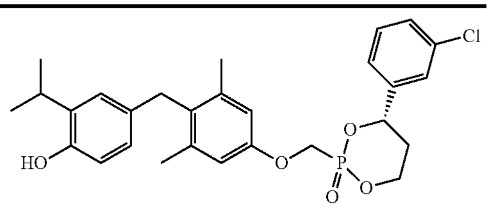 |
| 2 | 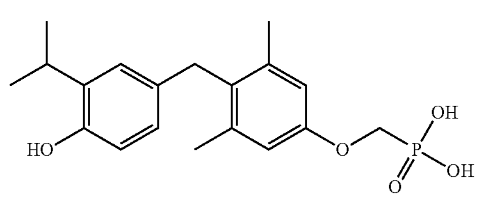 [SMILES: Cc1cc(OCP(=O)(O)O)cc(C)c1Cc1ccc(O)c(C(C)C)c1] |
| 3 | |
| 4 | |

In certain embodiments, the present invention provides a pharmaceutical preparation for use in a human patient in the treatment of X-ALD, comprising an effective amount of a compound of Formula I and one or more pharmaceutically acceptable excipients.

In certain embodiments, the subject is a mammal, e.g., a human.

Exemplary Pharmaceutical Compositions

In certain embodiments, the present invention provides pharmaceutical compositions comprising a compound of any preceding claim and a pharmaceutically acceptable carrier.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician having ordinary skill in the art can readily determine and prescribe the therapeutically effective amount of the pharmaceutical composition required. For example, the physician could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al., (1996) Harrison's Principles of Internal Medicine 13 ed., 1814-1882, herein incorporated by reference).

In general, a suitable dose of an active compound used in the compositions and methods of the invention will be that amount of the compound that is the lowest dose effective to produce a therapeutic effect. Such an effective dose will generally depend upon the factors described above.

In certain embodiments, the thyroid hormone receptor beta agonist may be administered daily. If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In certain embodiments, the thyroid hormone receptor beta agonist may be administered every other day.

In some embodiments, the thyroid hormone receptor beta agonist is administered intermittently to a subject on a multiple daily dosing schedule. In such embodiments, the compound is administered on at least two days and on as many as five different days. In one aspect of multiple daily dosing schedules, the compound is administered to the subject on consecutive days, such as from two to five consecutive days. In certain embodiments, the compound is administered to the subject for 3 consecutive days with one day without a dose before repeating the dosing cycle.

In certain embodiments, the thyroid hormone receptor beta agonist may be administered daily, every other day, or intermittently for two, three, or four months followed by a period of time when the thyroid hormone receptor beta agonist is not administered (e.g., a drug holiday). In some embodiments, the period of time when thyroid hormone receptor beta agonist is not administered may be from about 56 days to about 5 days, such as about 49 days, such as about 42 days, such as about 35 days, such as about 28 days, such as about 21 days, such as about 14 days, or such as about 7 days, preferably 28 days. In some embodiments, the period of time when thyroid hormone receptor beta agonist is not administered may be from about 2 months to about 1 week, such as 1 month.

In certain embodiments, the thyroid hormone receptor beta agonist may be administered at a dose between about 1 mg and about 100 mg per day, such as between about 1 mg and about 50 mg per day, such as between about 1 mg and about 25 mg per day, such as between about 1 mg and about 20 mg per day, such as between about 5 mg and 25 mg per day, such as between about 5 mg and about 20 mg per day, or about 5 mg and about 15 mg per day. In certain embodiments, a thyroid hormone receptor beta agonist may be administered at a dose of 100 mg/day, 50 mg/day, 25 mg/day, 20 mg/day, 15 mg/day, 10 mg/day, 5 mg/day, or 1 mg/day.

In certain embodiments, a thyroid hormone receptor beta agonist may be administered at a dose between about 1 mg and about 100 mg every other day, such as between about 1 mg and about 50 mg every other day, such as between about 1 mg and about 25 mg every other day, such as between about 1 mg and about 20 mg every other day, such as between about 5 mg and 25 mg every other day, such as between about 5 mg and about 20 mg every other day, or about 5 mg and about 15 mg every other day. In certain embodiments, a thyroid hormone receptor beta agonist may be administered at a dose of 100 mg every other day, 50 mg every other day, 25 mg every other day, 20 mg every other day, 15 mg every other day, 10 mg every other day, 5 mg every other day, or 1 mg every other day.

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "C$_{x-y}$" when used in conjunction with a chemical moiety, such as, acyl, acyloxy, alkyl, alkenyl, alkynyl, or alkoxy is meant to include groups that contain from x to y carbons in the chain. For example, the term "C$_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-trifluoroethyl, etc. C$_0$ alkyl indicates a hydrogen where the group is in a terminal position, a bond if internal. The terms "C$_{2-y}$alkenyl" and "C$_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

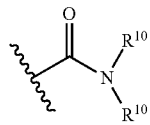

wherein each R$^{10}$ independently represent a hydrogen or hydrocarbyl group, or two R$^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

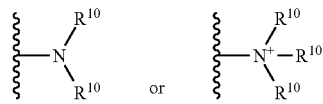

wherein each R$^{10}$ independently represents a hydrogen or a hydrocarbyl group, or two R$^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

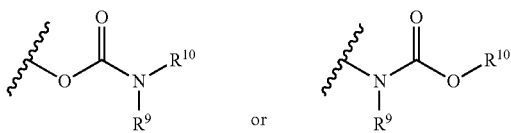

wherein R$^9$ and R$^{10}$ independently represent hydrogen or a hydrocarbyl group, such as an alkyl group, or R$^9$ and R$^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O—heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

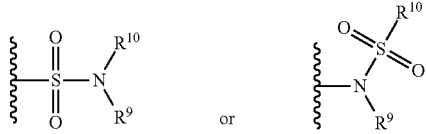

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

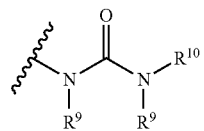

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

Standard prodrugs are formed using groups attached to functionality, e.g., HO—, HS—, HOOC—, R$_2$N—, associated with the a thyroid hormone receptor beta agonist, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Standard prodrugs of phosphonic acids are also included and may be represented by $R^1$ in formula I. The groups illustrated are exemplary, not exhaustive, and one skilled in the art could prepare other known varieties of prodrugs. Such prodrugs of the compounds of formula I fall within the scope of the present invention. Prodrugs must undergo some form of a chemical transformation to produce the compound that is biologically active or is a precursor of the biologically active compound. In some cases, the prodrug is biologically active usually less than the drug itself, and serves to improve efficacy or safety through improved oral bioavailability, pharmacodynamic half-life, etc.

The term "prodrug ester" as employed herein includes, but is not limited to, the following groups and combinations of these groups:

[1] Acyloxyalkyl esters which are well described in the literature (Farquhar et al., *J. Pharm. Sci.* 72, 324-325 (1983)) and are represented by formula A

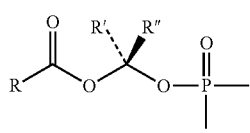

Formula A wherein R, R', and R" are independently H, alkyl, aryl, alkylaryl, and alicyclic; (see WO 90/08155; WO 90/10636).

[2] Other acyloxyalkyl esters are possible in which an alicyclic ring is formed, such as is shown in formula B. These esters have been shown to generate phosphorus-containing nucleotides inside cells through a postulated sequence of reactions beginning with desertification and followed by a series of elimination reactions (e.g., Freed et al., *Biochem. Pharm.* 38: 3193-3198 (1989)).

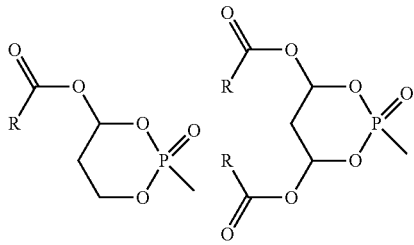

Formula B wherein R is —H, alkyl, aryl, alkylaryl, alkoxy, aryloxy, alkylthio, arylthio, alkylamino, arylamino, cycloalkyl, or alicyclic.

[3] Another class of these double esters known as alkyloxycarbonyloxymethyl esters, as shown in formula A, where R is alkoxy, aryloxy, alkylthio, arylthio, alkylamino, and arylamino; R', and R" are independently H, alkyl, aryl, alkylaryl, and alicyclic, have been studied in the area of β-lactam antibiotics (Tatsuo Nishimura et al. *J. Antibiotics*, 1987, 40(1), 81-90; for a review see Ferres, H., *Drugs of Today*, 1983, 19, 499.). More recently Cathy, M. S., et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

[4] Aryl esters have also been used as phosphonate prodrugs (e.g. Erion, DeLambert et al., *J. Med. Chem.* 37: 498, 1994; Serafinowska et al., *J. Med. Chem.* 38: 1372, 1995). Phenyl as well as mono and poly-substituted phenyl proesters have generated the parent phosphonic acid in studies conducted in animals and in man (Formula C). Another approach has been described where Y is a carboxylic ester ortho to the phosphate. Khamnei and Torrence, *J. Med. Chem.*; 39:4109-4115 (1996).

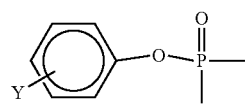

Formula C wherein Y is H, alkyl, aryl, alkylaryl, alkoxy, acyloxy, halogen, amino, alkoxycarbonyl, hydroxy, cyano, and alicyclic.

[5] Benzyl esters have also been reported to generate the parent phosphonic acid. In some cases, using substituents at the para-position can accelerate the hydrolysis. Benzyl analogs with 4-acyloxy or 4-alkyloxy group [Formula D, X=H, OR or O(CO)R or O(CO)OR] can generate the 4-hydroxy compound more readily through the action of enzymes, e.g. oxidases, esterases, etc. Examples of this class of prodrugs are described in Mitchell et al., *J. Chem. Soc. Perkin Trans.* I 2345 (1992); Brook, et al. WO 91/19721.

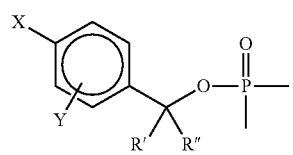

Formula D wherein X and Y are independently H, alkyl, aryl, alkylaryl, alkoxy, acyloxy, hydroxy, cyano, nitro, perhaloalkyl, halo, or alkyloxycarbonyl; and R' and R" are independently H, alkyl, aryl, alkylaryl, halogen, and alicyclic.

[6] Thio-containing phosphonate proesters have been described that are useful in the delivery of FBPase inhibitors to hepatocytes. These proesters contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., *Antiviral Res.*, 22: 155-174 (1993)). Thioesters will also generate free thiolates after esterase-mediated hydrolysis. Benzaria, et al., *J. Med. Chem.*, 39:4958 (1996). Cyclic analogs are also possible and were shown to liberate phosphonate in isolated rat hepatocytes.

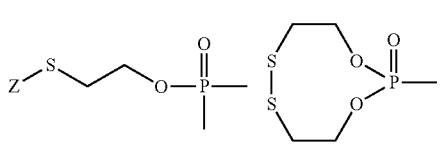

Formula E wherein Z is alkylcarbonyl, alkoxycarbonyl, arylcarbonyl, aryloxycarbonyl, or alkylthio.

Other examples of suitable prodrugs include proester classes exemplified by Biller and Magnin (U.S. Pat. No. 5,157,027); Serafinowska et al. (*J. Med. Chem.* 38, 1372 (1995)); Starrett et al. (*J. Med. Chem.* 37, 1857 (1994)); Martin et al. *J. Pharm. Sci.* 76, 180 (1987); Alexander et al., *Collect. Czech. Chem. Commun,* 59, 1853 (1994)); and EPO patent application 0 632 048 A1. Some of the structural classes described are optionally substituted, including fused lactones attached at the omega position (formulae E-1 and E-2) and optionally substituted 2-oxo-1,3-dioxolenes attached through a methylene to the phosphorus oxygen (formula E-3) such as:

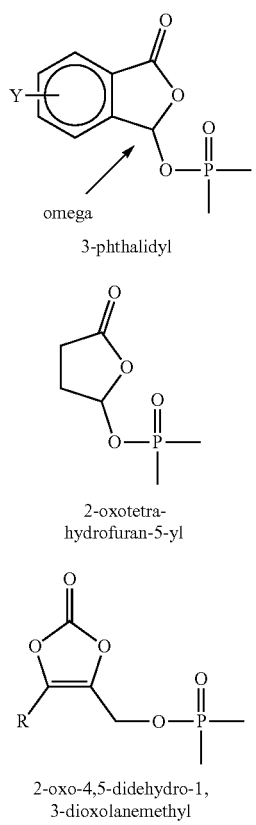

wherein R is —H, alkyl, cycloalkyl, or alicyclic; and wherein Y is —H, alkyl, aryl, alkylaryl, cyano, alkoxy, acyloxy, halogen, amino, alicyclic, and alkoxycarbonyl.

The prodrugs of Formula E-3 are an example of "optionally substituted alicyclic where the cyclic moiety contains a carbonate or thiocarbonate."

[7] Propyl phosphonate proesters can also be used to deliver FBPase inhibitors into hepatocytes. These proesters may contain a hydroxyl and hydroxyl group derivatives at the 3-position of the propyl group as shown in formula F. The R and X groups can form a cyclic ring system as shown in formula F. One or more of the oxygens of the phosphonate can be esterified.

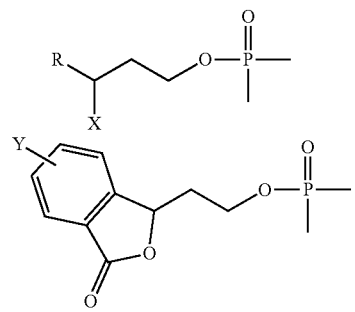

wherein
R is alkyl, aryl, heteroaryl;
X is hydrogen, alkylcarbonyloxy, alkyloxycarbonyloxy; and
Y is alkyl, aryl, heteroaryl, alkoxy, alkylamino, alkylthio, halogen, hydrogen, hydroxy, acyloxy, amino.

[8] Phosphoramidate derivatives have been explored as phosphate prodrugs (e.g., McGuigan et al., *J. Med. Chem.,* 1999, 42: 393 and references cited therein) as shown in Formula G and H.

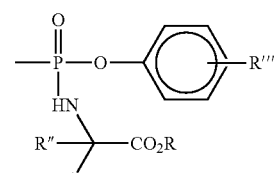

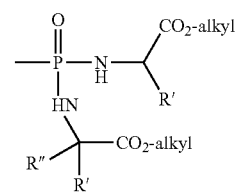

Cyclic phosphoramidates have also been studied as phosphonate prodrugs because of their speculated higher stability compared to non-cyclic phosphoramidates (e.g. Starrett et al., *J. Med. Chem.,* 1994, 37: 1857.

Another type of nucleotide prodrug was reported as the combination of S-acyl-2-thioethyl ester and phosphoramidate (Egron et al., *Nucleosides & Nucleotides,* 1999, 18, 981) as shown in Formula K.

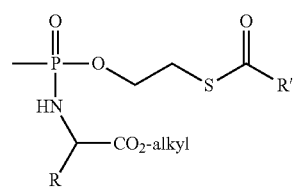

Other prodrugs are possible based on literature reports such as substituted ethyls for example, bis(trichloroethyl) esters as disclosed by McGuigan, et al. *Bioorg Med. Chem. Lett.,* 3:1207-1210 (1993), and the phenyl and benzyl combined nucleotide esters reported by Meier, C. et al. *Bioorg. Med. Chem. Lett.,* 7:99-104 (1997).

The structure

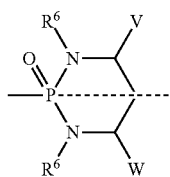

has a plane of symmetry running through the phosphorus-oxygen double bond when $R^6=R^6$, $V=W$, $W'=H$, and V and W are either both pointing up or both pointing down. The same is true of structures where each —$NR^6$ is replaced with —O—.

EXAMPLES

The invention now being generally described will be more readily understood by reference to the following examples which are included merely for purposes of illustration of the certain aspects and embodiments of the present invention, and are not intended to limit the invention in any way.
Experimental Procedures Human primary fibroblasts. Human skin fibroblasts were obtained from X-ALD patients through the Neurology Outpatient Clinic of the Academic Medical Center. Written informed consent was received from each patient. X-ALD diagnosis was confirmed by VLCFA and ABCD1 mutation analysis. Control fibroblasts were obtained from male anonymous volunteers with written informed consent. Fibroblasts were cultured in Dulbecco's modified Eagle's medium (DMEM) with L-glutamine and 4.5 g/L glucose, supplemented with 10% fetal calf serum, 2.5 mM HEPES, 100 U/ml penicillin and 100 U/ml streptomycin. Cells were cultured at 37° C. in a humidified 5% $CO_2$ atmosphere. All fibroblast cell lines used were tested routinely for mycoplasma. All tests were negative.

Preparation of stock solutions. 10 mM stock solutions in DMSO were prepared by weighing the amount of compound (1 and 3 and their respective active metabolites, 2 and 4) as indicated in Table 2. Stock solutions were stored at room temperature in the dark. For each incubation, the amount of tissue culture medium needed was calculated and a stock solution of tissue culture medium with the final concentration of the to-be-tested compound was prepared. Tissue culture medium was removed from the cells, cells were washed once with PBS and the tissue culture medium with the compounds was added. If an experiment lasted longer than three days, the tissue culture medium and compounds were refreshed (using a fresh preparation) after three days until the end of the experiment.

TABLE 2

| Compound | Assay Concentration | | | MW | 100X stock solution 10 mM | |
|---|---|---|---|---|---|---|
| | Low | Medium | High | | | |
| 2 | 100 nM | 1 µM | 10 µM | 364 | 3.64 | mg/mL |
| 4 | 100 nM | 1 µM | 10 µM | 412 | 4.12 | mg/mL |
| 1 | 1 µM | 10 µM | 100 µM | 515 | 5.15 | mg/mL |
| 3 | 1 µM | 10 µM | 100 µM | 641 | 6.41 | mg/mL |

Quantitative PCR (qPCR) analysis. Total RNA was isolated with TRIreagent (Sigma-Aldrich) according to manufactures guidelines with the addition of an extra DNase treatment (Promega). Nanodrop 2000 (Thermo Fisher Scientific) was used for the quantification and qualification of the RNA samples. cDNA was synthesized using the first-strand cDNA synthesis kit (Roche). LightCycler 480 SYBR Green I Master (Roche) was used for qPCR analysis. For data analysis, Light Cycler 480 software release 1.5.0 and LinRegPCR version 2014.5 (Ramakers et al., *Neuroscience Letters* 339: 62-66 (2003)) were used. The geometric mean of the expression levels of two validated housekeeping genes RPS14 and H3F3A (their expression levels are unaffected by the treatment) was used for normalization of the qPCR data.

The effect of treatment on $D_3$-C22:0 beta-oxidation in intact cells. Peroxisomal beta-oxidation activity was measured essentially as described by incubating cells with 30 µM deuterium-labeled C22:0 (D3-C22:0) (Kemp et al., *Clinical Chemistry* 50: 1824-1826 (2004)). Cells were seeded at approximately 40% confluency in T75 flasks in DMEM. The next day, medium was replaced with medium containing 30 µM D3-C22:0 and assayed compounds at their final concentration. Final DMSO concentration in the tissue culture medium did not exceed 1%. Each 72 h, the tissue culture medium and compounds was refreshed. At the end of the experiment cells were harvested and VLCFA analyzed as described (Valianpour et al., *Molecular Genetics and Metabolism*, 79: 189-196 (2003)).

The effect of treatment on D3-C26:0 synthesis in intact cells. The effect of certain compounds of the invention on the synthesis of D3-C26:0 from D3-C22:0 was measured in cultured skin fibroblasts from controls and X-ALD patients. Cells were seeded at approximately 40% confluency in T75 flasks in DMEM. The next day, medium was replaced with medium containing 30 µM D3-C22:0 and the assayed compounds at their final concentration. Final DMSO concentration in the tissue culture medium did not exceed 1%. Each 72 h, the tissue culture medium and compounds was refreshed. At the end of the experiment cells were harvested and VLCFA analyzed as described (Valianpour et al., *Molecular Genetics and Metabolism*, 79: 189-196 (2003)).

VLCFA measurement. VLCFA were analyzed by electrospray ionization mass spectrometry (ESI-MS) as described (Valianpour et al., *Molecular Genetics and Metabolism*, 79: 189-196 (2003)).

Example 1—Assessment of Varying Treatment Dosages

Two different X-ALD fibroblast cell lines were incubated in duplicate with four compounds at three dosages as highlighted in Table 3.

TABLE 3

| Compound | Low | Medium | High |
|---|---|---|---|
| 2 | 100 nM | 1 µM | 10 µM |
| 4 | 100 nM | 1 µM | 10 µM |
| 1 | 1 µM | 10 µM | 100 µM |
| 3 | 1 µM | 10 µM | 100 µM |

Both X-ALD cell lines that were incubated with 100 µM 1 and 3 were dead within 24 hours. This strongly indicates that 1 and 3 are toxic at 100 µM. After 72 hours the cells that had received 0.1, 1 or 10 µM 2 or 4 or 0.1 or 10 µM 1 or 3 looked healthy by judging their proliferation and morphology.

After 72 h, cells were harvested and mRNA was isolated for QPCR analysis. The effect of compounds on ABCD2 expression was compared with the ABCD2 expression level in the untreated (DMSO) cell lines as shown in FIG. 1. For all 4 tested compounds, 10 μM was most effective. At this concentration, no negative impact of proliferation and cell morphology were observed.

Example 2—Assessment after Extended Incubation

4 X-ALD cell lines were incubated with 10 μM of 4 compounds 1, 2, 3, and 4. The effect of treatment on ABCD2 expression was analyzed at day 3 and day 10. For the 10 day incubation, tissue culture medium and compounds were refreshed at day 3 and day 6.

Days 3, 6 and 10: all cells look healthy, proliferation is normal, morphology is normal. Nothing unusual noted. After 3 days, cells were harvested and mRNA was isolated for QPCR analysis. After 10 days, cells were harvested and mRNA was isolated for QPCR analysis. For all samples, cDNA synthesis and QPCR was done on the same day.

Figure 2:
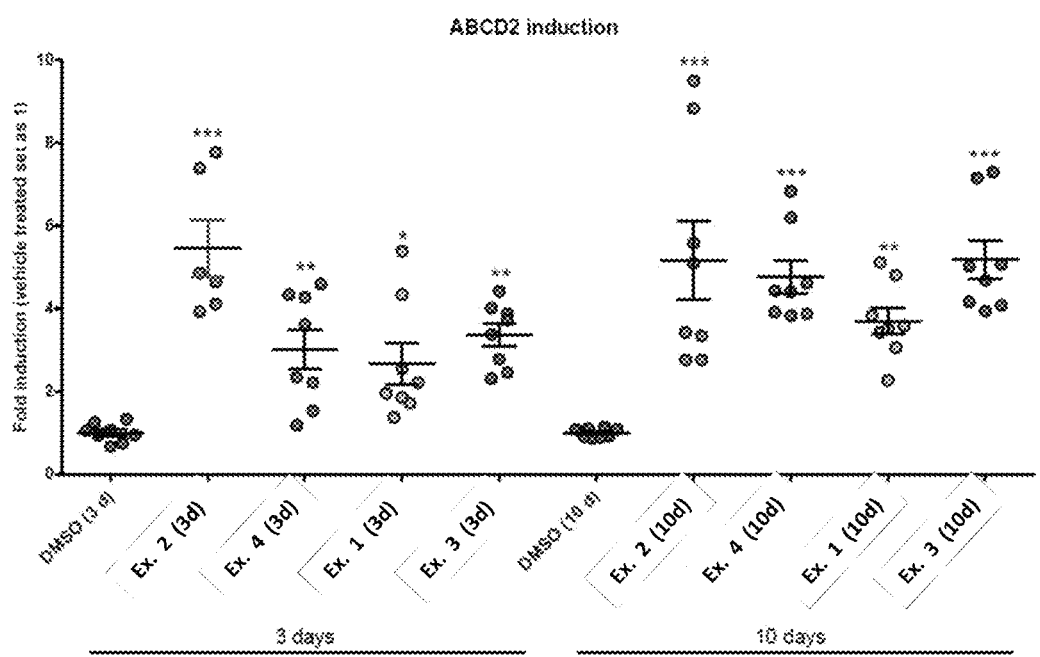
FIG. 2 is a plot showing the qPCR analysis of the assayed compounds at 3 days and 10 days of incubation.
Figure 3:
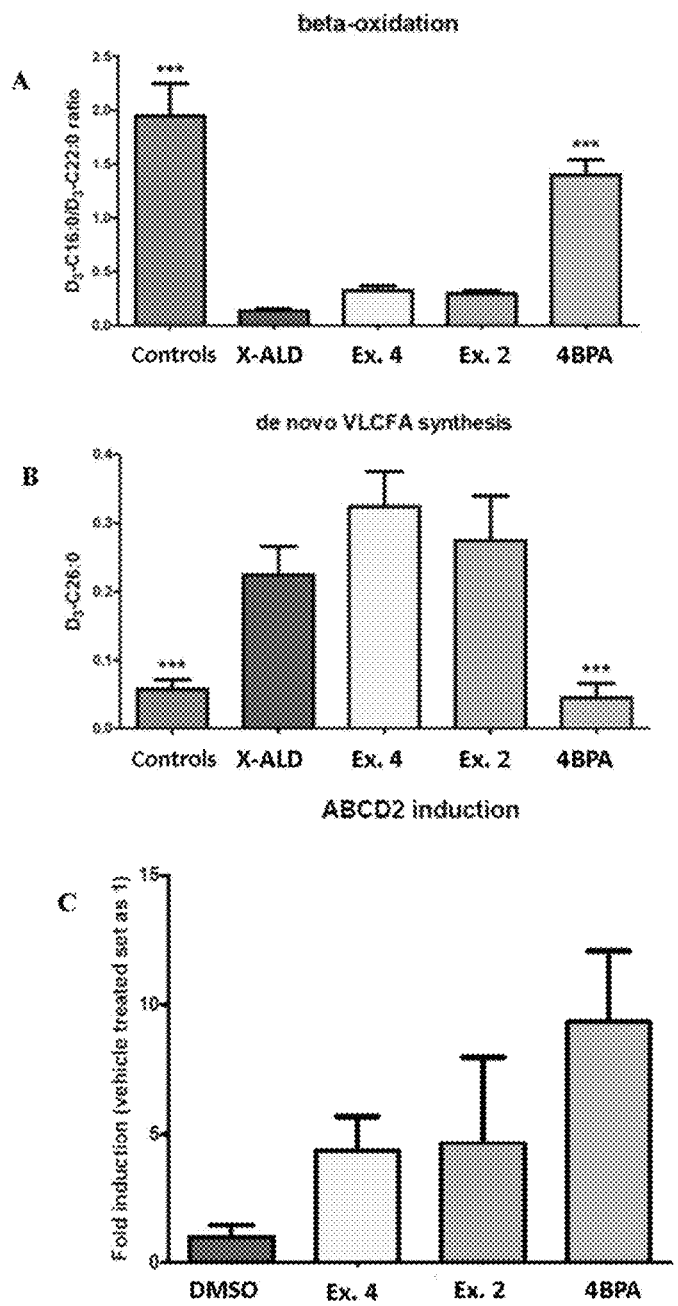
FIG. 3 includes three panels (Panels A-C) showing the effects of incubating X-ALD cell lines with Compounds 2 and 4 on VLCFA beta-oxidation (Panel A), D3C26:0 synthesis (Panel B), and ABCD2 induction (Panel C).

The effect of compound treatment on ABCD2 expression was compared with the ABCD2 expression level in the untreated (DMSO) cell lines at day 3 and day 10 as a shown in FIG. 2. Prolonged exposure resulted in a comparable effect on ABCD2 induction.

Figure 4:
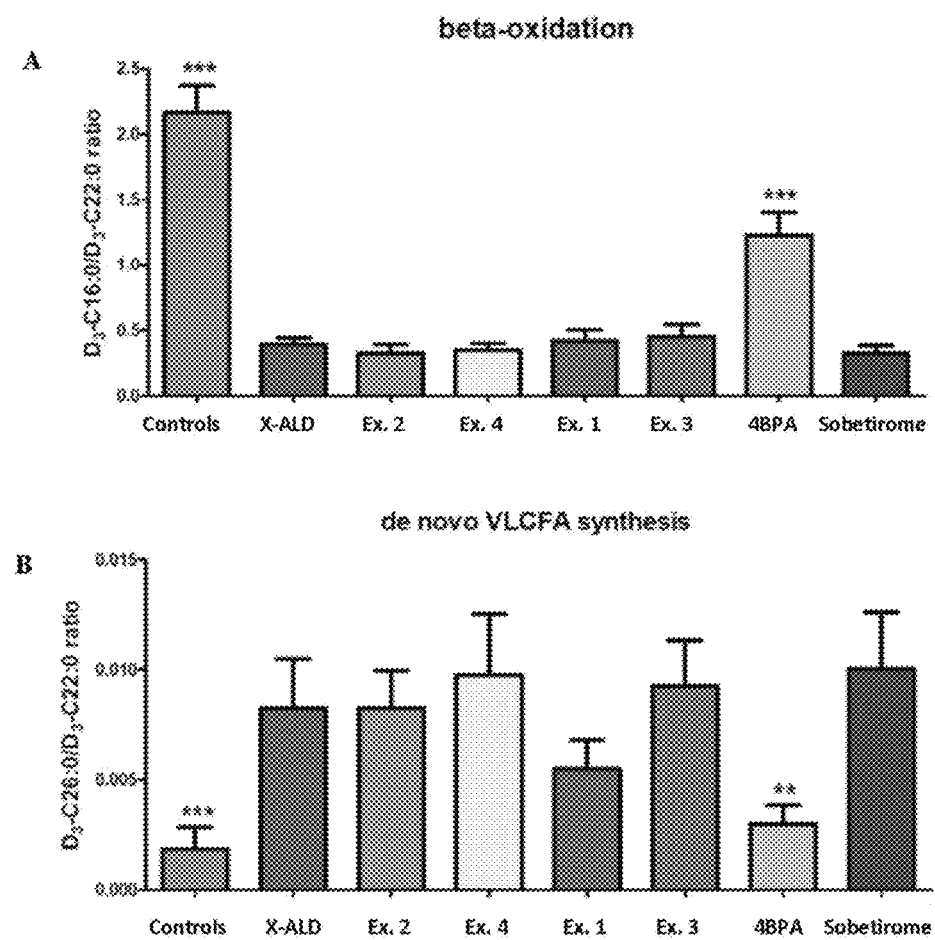
FIG. 4 includes two panels (Panels A and B) showing the effects of incubating X-ALD cell lines for 10 days with compounds 1, 2, 3, and 4 and 4-PBA and sobetirome on VLCFA beta-oxidation (Panel A) and de novo VLCFA synthesis (Panel B).

Example 3-10 Day Treatment on De Novo VLCFA Synthesis 5 different X-ALD cell lines were incubated for 6 days with compounds 1, 2, 3, and 4 at 10 μM, 5 mM 4PBA (sodium 4-phenylbutyrate), or 0.1 μM sobetirome. On Day 6, 30 μM D3C22:0 was added to assess the effect of treatment on beta-oxidation and de novo D3C26:0 synthesis. 6 untreated control cells as well as 5 different untreated X-ALD cells were included to allow assessment of the treatment effect. The total set consisted of 41 experiments In untreated X-ALD cells, the beta-oxidation capacity is reduced by ~80% and de novo C26:0 synthesis increased by ~4-fold as shown in FIG. 4. The positive control, 4PBA, restored beta-oxidation to ~50% of controls and normalized VLCFA synthesis to near normal levels. The positive control, sobetirome, did not show any beneficial effect on VLCFA beta-oxidation or de novo synthesis.

Compound 1, which was also the most active in experiment 3, resulted in an ~40% reduction in D3C26:0 de novo synthesis.

Figure 5:
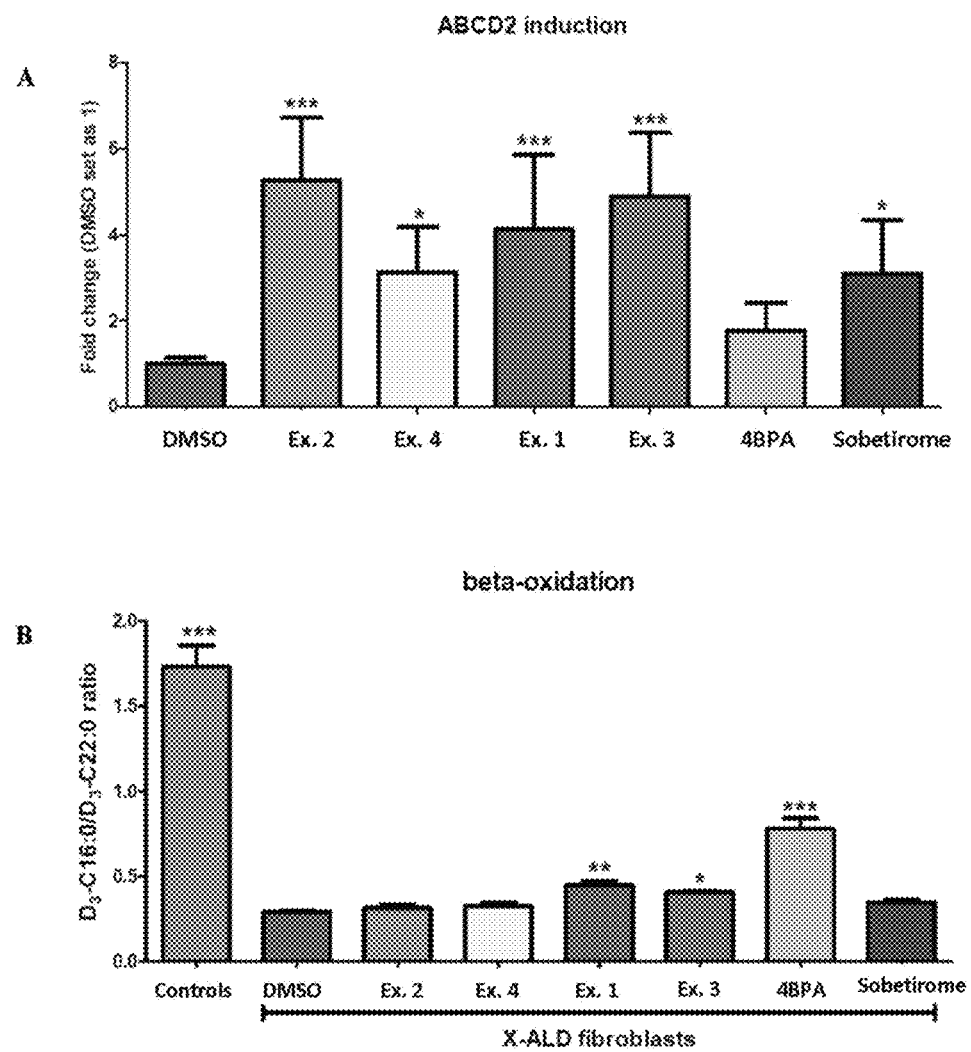
FIG. 5 includes three panels (Panels A-C) showing the effects of incubating X-ALD cell lines for 3 days with compounds 1, 2, 3, and 4 and 4-PBA, and sobetirome on ABCD2 induction (Panel A), VLCFA beta-oxidation (Panel B), and de novo VLCFA synthesis (Panel C).
Figure 5:
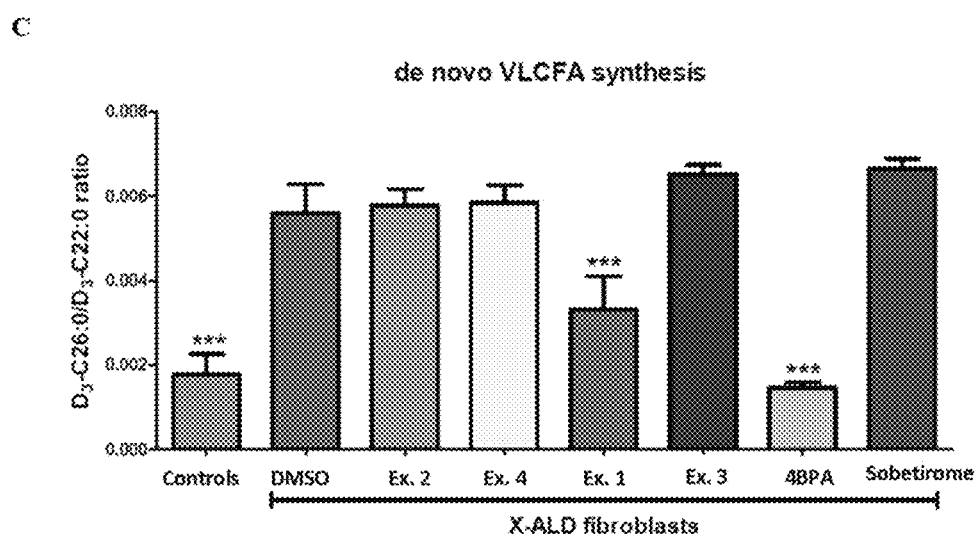

Example 4-3 Day Treatment on De Novo VLCFA Synthesis 3 different X-ALD cell lines were incubated overnight for 16 hours with compounds 1, 2, 3 and 4 at 10 μM, 5 mM 4PBA, or 0.1 μM sobetirome. After 16 hours, tissue culture medium was replaced with medium containing the above compounds and 30 μM D3C22:0 was added to assess the effect of treatment on beta-oxidation and de novo D3C26:0 synthesis. 6 untreated control cells as well as 3 different untreated X-ALD cells were included to allow assessment of the treatment effect. The total set consisted of 27 experiments. Simultaneously cells were cultured for QPCR analysis that received the same treatment. See FIG. 5.

Example 5—Multi Dose Assessment in Rodents (Prophetic)

Two to four groups of 12 ABCD1 knockout male mice that are at least 6 weeks old will be administered either compound 1 or compound 3 in a formulation comprising 0.5% carboxymethyl cellulose and water at a dose of 3-5 mg/kg and 10 mg/kg. A homogenous suspension will be obtained by sonication in a bath sonicator for about 20 minutes at room temperature. Mice will be administered the homogenous suspension by daily intraperitoneal injection for 6 weeks.

After 6 weeks, changes in ABCD2 expression levels and VLCFA levels will be assessed along with plasma and tissue levels.

Example 6—Evaluation of Compound 3 in an In Vivo Model of X-ALD

Materials and Methods

Animals. Male ABCD1−/− mice were developed using the Taconic 129SvEv background strain. Animals were housed 3-4/cage under a 12-hour lighting cycle (7 AM-7 PM light) and controlled temperature (22° C.) in the rodent facility. They were fed standard mouse chow and had access to drinking water ad libitum. Mice were between 2 and 3 months of age at the beginning of each study.

Study Protocol. Mice were injected once daily intraperitoneal with either drug or vehicle. For blood collection, ~50 μL of blood was obtained by facial vein puncture using a sterile lancet. Blood was collected in a 1.5 ml microcentrifuge tube containing dried dipotassium EDTA and mixed by gentle inversion at least ten times before storing at −20° C. Blood was obtained in this manner following two, four, and six weeks of treatment. Following blood collection at six weeks, animals were sacrificed by cervical dislocation. Additional blood for preparation of plasma was obtained via cardiac puncture, and blood placed in Microtainer tubes. Brain, spinal cord, adrenal glands, testis, and liver were excised and snap frozen in liquid nitrogen for future analyses.

Results

Figure 6:
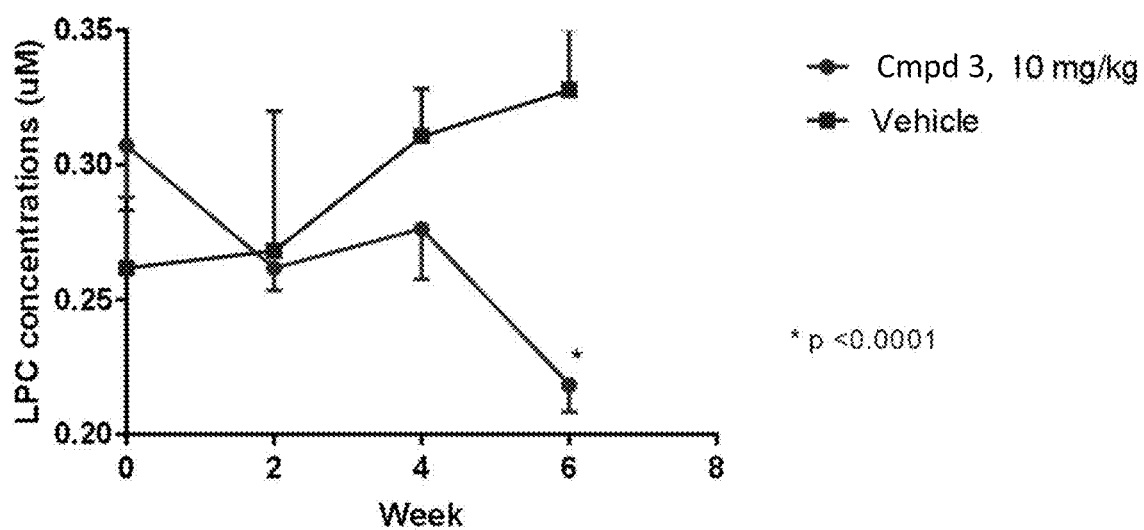
FIG. 6 is a line graph depicting data showing the time course of C26:0-LPC levels in whole blood from the initial cohort.

An initial cohort of 16 mice were randomized 3:1 to receive compound 3 or placebo, once daily for six weeks. The results of this initial cohort are presented in FIG. 6 and summarized in Table 4. Mice receiving compound 3 demonstrated rapid reductions in whole blood C26:0-LPC levels in as little as two weeks following initiation of dosing. Treated animals continued to experience progressive declines in C26:0-LPC through six weeks. Control animals, by comparison, demonstrated no reductions in mean C26:0-LPC at any time point. Following the six week treatment period, animals receiving compound 3 demonstrated a 40% reduction in whole blood C26:0-LPC levels relative to vehicle controls ($p<0.0001$).

TABLE 4

Mean Blood Levels of C26:0-LPC

| Week | C26:0-LPC Levels (μM) | | |
|---|---|---|---|
| | 2 | 4 | 6 |
| Vehicle | 0.268 | 0.311 | 0.214 |
| Compound 3 | 0.262 | 0.276 | 0.356 |
| % Difference versus Vehicle | 0% | −11% | −40% |
| p-value (versus Vehicle) | NS | NS | <0.0001 |
| Difference in Mean Change from Baseline | −0.052 | −0.081 | −0.188 |

Similar results were obtained with other VLCFA-LPC measurements; highly statistically significant reductions in mean levels of C20:0-, C22:0-, and C24:0-LPC were observed.

Based on the encouraging results of the initial cohort, a second, larger, cohort was evaluated. A total of 20 mice were randomized 1:1 to receive daily compound 3 or vehicle, by IP administration, for six weeks.

Figure 7:
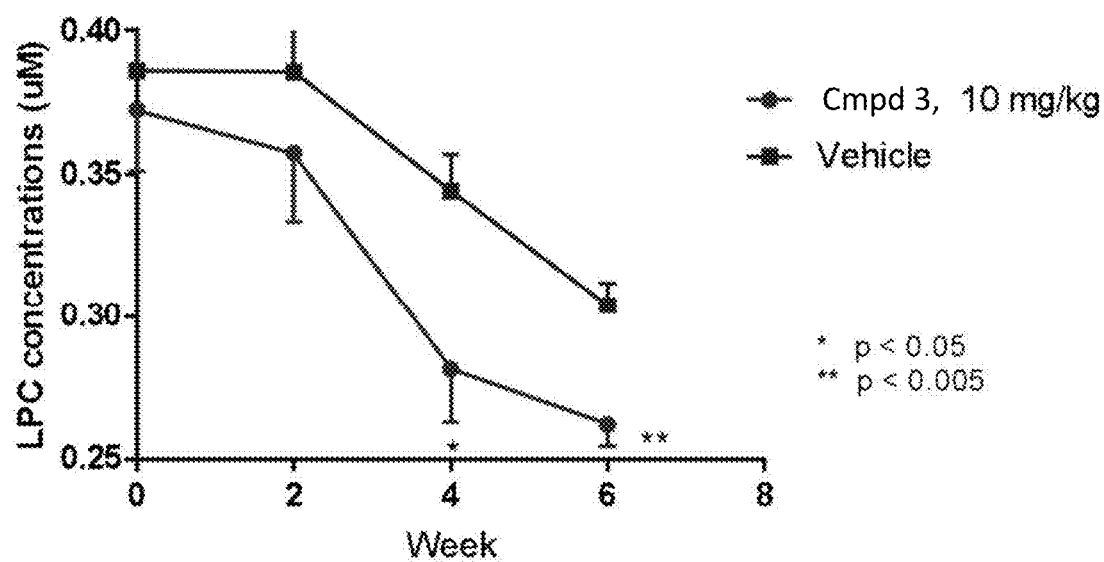
FIG. 7 is a line graph depicting data showing the time course of C26:0-LPC levels in whole blood from the second cohort.

Results from the second cohort confirmed the initial data, with treated mice demonstrating significant and progressive reductions in whole blood VLCFA levels relative to controls. FIG. 7 shows the time course of changes in C26:0-LPC levels through the course of treatment. Animals receiving compound 3 demonstrated a statistically significant drop in VLCFAs, both in terms of comparison to vehicle at Week 6, and in terms of change from baseline (see FIG. 8 and Table 5). Similar changes were noted for the other VLCFAs analyzed (C20:0, C22:0, C24:0). Interestingly, a vehicle effect was observed in this cohort that was not observed in the prior experiment. This could be the result of the lipid-based nature of the vehicle, via a mechanism similar to that observed with agents such as Lorenzo's Oil.

Figure 8:
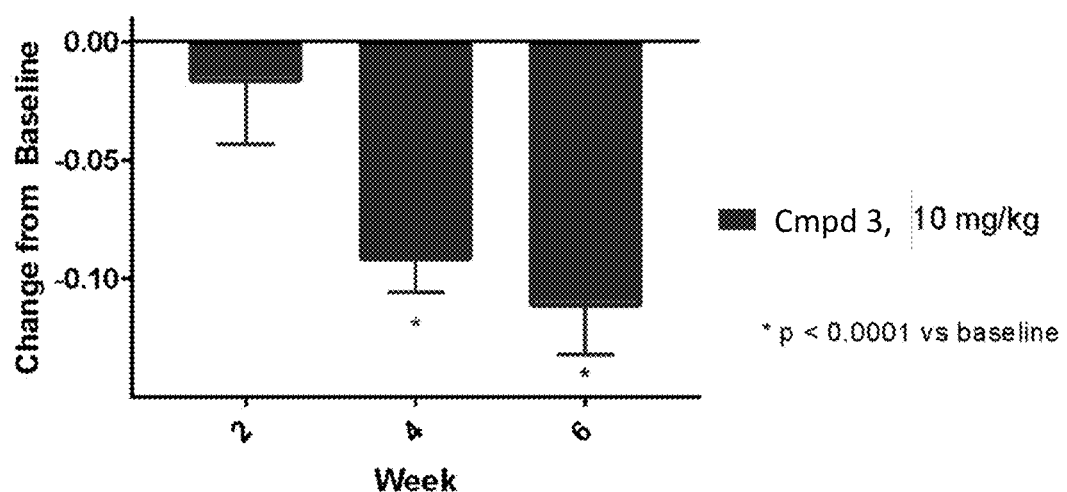
FIG. 8 is a bar graph depicting data showing the change from baseline C26:0 of compound 3 in whole blood.

Animals receiving compound 3 demonstrated an approximately 0.11 µM reduction in whole blood C26:0-LPC levels following six weeks of treatment (FIG. 8). The change from baseline was significant at weeks four and six. Relative to vehicle-treated animals, treatment with compound 3 led to a 52% reduction in C26:0-LPC at six weeks (p<0.005, Table 5).

TABLE 5

Least Squares Mean Change from Baseline Whole Blood C26:0-LPC Levels in compound 3 Treated Mice vs Vehicle

| Week | VLCFA-LPC (µM) | | |
|---|---|---|---|
| | 2 | 4 | 6 |
| Vehicle | −0.0052 | −0.036 | −0.076 |
| compound 3 | −0.021 | −0.096 | −0.12 |
| p-value (versus Vehicle) | NS | <0.01 | <0.005 |

During the second cohort study, blood was obtained as described in the Methods section. At the six week time point sufficient blood was collected to permit plasma VLCFA analyses at weeks two, four and six. The results of the plasma analyses are presented in FIG. 7 and Table 6. Plasma is considered by many to be a more reliable measurement of VLCFA levels, because of reduced analytical interference from other analytes, as well as reduced variability of the measurements.

Figure 9:
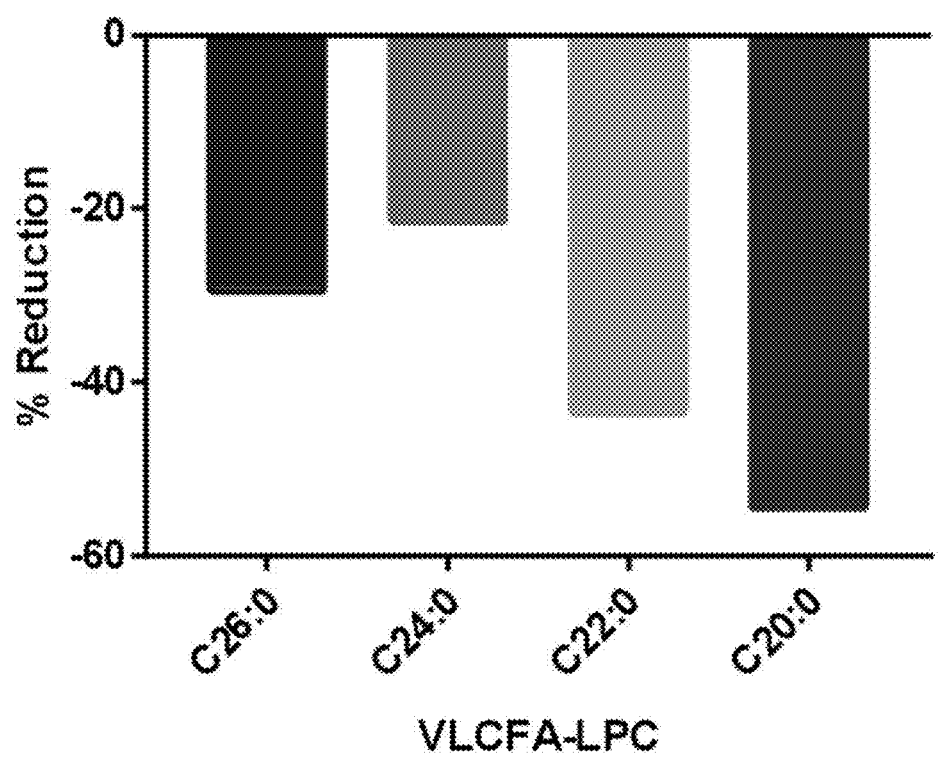
FIG. 9 is a bar graph depicting data showing the time course of C26:0-LPC levels in plasma from the initial cohort.

As shown in FIG. 9 and Table 6, exposure to compound 3 led to reductions across a broad range of VLCFAs, including C26:0, C24:0, C22:0, and C20:0. These effects were highly statistically significant relative to vehicle-treated mice, and served to confirm the observations from whole blood, as well as the initial data generated in the first treatment cohort. Interestingly, a trend toward a decreasing impact on the longer chain analytes may suggest that compound 3's effect on shorter chain VLCFAs results in a reduced substrate pool for elongase enzymes.

TABLE 6

Percent Change in Mean Plasma LPC levels of compound 3 Treated Mice vs. Vehicle at Week 6.

| | VLCFA-LPC (µM) | | | |
|---|---|---|---|---|
| | C26:0 | C24:0 | C22:0 | C20:0 |
| Vehicle | 0.29 | 1.44 | 0.35 | 1.63 |
| compound 3 | 0.20 | 1.14 | 0.20 | 0.76 |
| % Difference | −29% | −21% | −43% | −54% |
| p-value | <0.0001 | <0.005 | <0.0001 | <0.0001 |

Discussion

Treatment of ABCD1 knockout mice with compound 3 for six weeks resulted in a reduction in all VLCFA-lyso-PC analytes measured in this experiment. The differences between compound 3-treated and vehicle-treated animals on the key C26:0-LPC analyte were significant at both the four and six week time points, and the effects were observed in both whole blood and plasma. The response to compound 3 appeared to be progressive; differences between treatment and vehicle effects on C26:0-LPC generally increased over the course of the study.

Significant reductions were also observed in change from baseline analyses. Treatment with compound 3 led to significant reductions from baseline in whole blood VLCFAs relative to vehicle at the four and six-week time points. In addition to the progressive treatment effect, differences relative to vehicle became more statistically significant over time.

Exposure to compound 3 resulted in broad effects on VLCFA levels. After six weeks of treatment, significant reductions in C20:0-, C22:0-, and C24:0-LPC were observed. A trend toward larger effects on shorter VLCFA chain lengths may suggest depletion of the elongase substrate pool, potentially leading to enhanced reductions in longer chain VLCFAs, such as C26:0, over time.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method for treating X-linked adrenoleukodystrophy, comprising administering to a subject a compound selected from:

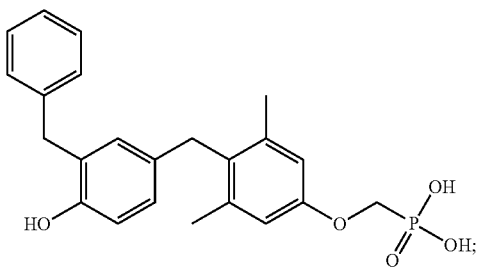 [SMILES: Cc1cc(OCP(=O)(O)O)cc(C)c1Cc1ccc(O)c(Cc2ccccc2)c1]

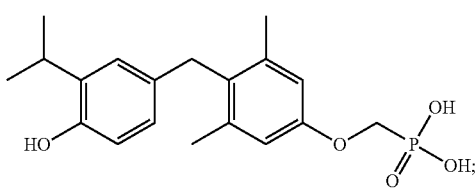

or a salt or ester thereof.

2. The method of claim 1, wherein the compound is

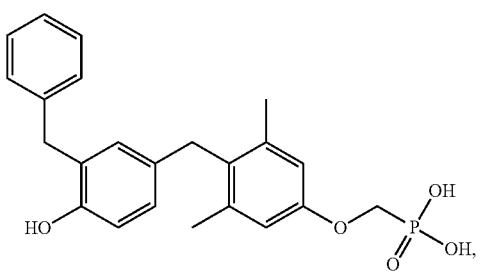

or a salt or ester thereof.

3. The method of claim 2, wherein the compound is

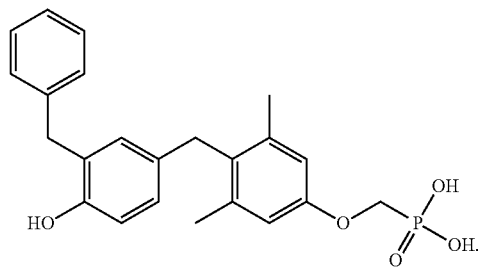 [SMILES: Cc1cc(OCP(=O)(O)O)cc(C)c1Cc1ccc(O)c(Cc2ccccc2)c1]

4. The method of claim 1, wherein the compound is

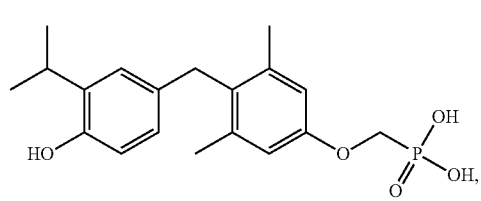 [SMILES: Cc1cc(OCP(=O)(O)O)cc(C)c1Cc1ccc(O)c(C(C)C)c1]

or a salt or ester thereof.

5. The method of claim 4, wherein the compound is

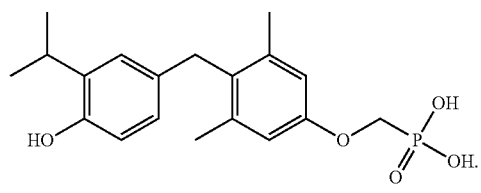 [SMILES: Cc1cc(OCP(=O)(O)O)cc(C)c1Cc1ccc(O)c(C(C)C)c1]

6. The method of claim 1, wherein the compound is administered daily, every other day, or intermittently for three months followed by a period of time of one month when the compound is not administered.

* * * * *